(12) United States Patent
Isobe

(10) Patent No.: US 7,015,002 B2
(45) Date of Patent: Mar. 21, 2006

(54) METHOD OF DETECTING BIOLOGICAL MOLECULES, AND LABELING DYE AND LABELING KIT USED FOR THE SAME

(75) Inventor: Shinichiro Isobe, 19-28-12, Yakatabaru 1-chome, Minami-ku, Fukuoka-shi 811-1351 (JP)

(73) Assignee: Shinichiro Isobe, Fukuoka (JP)

( * ) Notice: Subject to any disclaimer, the term of this patent is extended or adjusted under 35 U.S.C. 154(b) by 0 days.

(21) Appl. No.: 10/822,775

(22) Filed: Apr. 13, 2004

(65) Prior Publication Data

US 2005/0181380 A1 Aug. 18, 2005

(30) Foreign Application Priority Data

Dec. 24, 2003 (JP) ............................ 2003-427268
Mar. 31, 2004 (JP) ............................ 2004-105187

(51) Int. Cl.
*C12Q 1/68* (2006.01)
*C07H 21/00* (2006.01)
*C07H 21/02* (2006.01)
*C07H 21/04* (2006.01)

(52) U.S. Cl. ............................ 435/6; 435/6; 536/23.1; 536/24.3; 536/26.6

(58) Field of Classification Search .................... 435/6; 536/23.1, 24.3, 26.6
See application file for complete search history.

(56) References Cited

U.S. PATENT DOCUMENTS

| | | | |
|---|---|---|---|
| 5,206,149 A | 4/1993 | Oyama et al. | |
| 5,856,479 A | 1/1999 | Suzuki et al. | |
| 6,048,687 A | 4/2000 | Kenten et al. | |
| 6,358,634 B1 | 3/2002 | Igarashi et al. | |
| 6,451,457 B1 | 9/2002 | Taguchi | |
| 6,461,538 B1 | 10/2002 | Taguchi | |
| 6,461,747 B1 | 10/2002 | Okada et al. | |
| 6,482,640 B1 | 11/2002 | Tanaka et al. | |
| 6,528,187 B1 | 3/2003 | Okada | |
| 6,551,723 B1 | 4/2003 | Okada et al. | |
| 6,656,612 B1 | 12/2003 | Okada et al. | |
| 6,673,928 B1 | 1/2004 | Taguchi | |
| 6,696,182 B1 | 2/2004 | Yamada et al. | |
| 6,824,891 B1 | 11/2004 | Okada et al. | |
| 6,830,836 B1 | 12/2004 | Okada et al. | |
| 2002/0064782 A1 | 5/2002 | Shinoki et al. | |
| 2003/0037859 A1 | 2/2003 | Gupta et al. | |

FOREIGN PATENT DOCUMENTS

| | | |
|---|---|---|
| JP | 9-505464 | 6/1997 |
| JP | 2001-153870 | 6/2001 |
| JP | 2001-288197 | 10/2001 |
| JP | 2002-161135 | 6/2002 |
| JP | 2002-173673 | 6/2002 |
| JP | 2003-532790 | 11/2003 |

OTHER PUBLICATIONS

Iyer, V. R. et al., "The Transcriptional Program in the Response of Human Fibroblasts to Serum", *Science*, vol. 283, Jan. 1999, pp. 83-87.

*Primary Examiner*—Jezia Riley
(74) *Attorney, Agent, or Firm*—Wenderoth, Lind & Ponack L.L.P.

(57) ABSTRACT

The present invention provides a method of detecting a biological molecule. The method includes reacting a biological molecule sample with an organic EL-dye and measuring the fluorescence of the biological molecule sample labeled with the organic EL-dye. The method provides a highly sensitive method of detecting a biological molecule at lower cost.

12 Claims, 6 Drawing Sheets

(a) (b) (c) (d) (e)

Before purification

After purification (a)(b)(c)(d)(e)

METHOD OF DETECTING BIOLOGICAL MOLECULES, AND LABELING DYE AND LABELING KIT USED FOR THE SAME

BACKGROUND OF THE INVENTION

1. Field of the Invention

The present invention relates to a method of detecting a biological molecule such as nucleic acids, proteins, peptides, saccharides and the like using a fluorescence dye, and a labeling dye and a labeling kit used for the detection method.

2. Background Art

Recently, post genome researches have been intensively and world widely done aiming for specific gene analysis technologies, gene therapies and tailor made medical treatments. As for the gene analysis technology, a method of detecting DNA using a DNA microarray, for example, is used. According to this detection method, simultaneous analysis of expression, functionality, mutation and the like of a plurality of genes can be conducted simply and quickly.

In the detection method using a DNA microarray, DNA chips obtained by spot-fixing many sequences (probe nucleic acids) of DNA or oligonucleotide on a substrate made of glass, silicon or the like are used. By hybridization of a probe nucleic acid fixed on a substrate with a labeled sample RNA or DNA (target nucleic acid), a labeled nucleic acid having base sequence complimentary to that of the probe nucleic acid is selectively bound to the probe nucleic acid. After drying of the microarray, the fluorescence intensity of the labeled target nucleic acid is measured.

A fluorescence dye is widely used for labeling. High fluorescence intensity, emission even under dry conditions (solid conditions), water solubility, and the like are required for the fluorescence dye. As the fluorescence dye, for example, Cy3 and Cy5 are used (see, e.g., Science 283, 1 Jan. 1999, pp. 83–87).

SUMMARY OF THE INVENTION

However, although Cy3 and Cy5 manifest high fluorescence intensity and have a merit of emission even in solid state, they are very expensive, leading inevitably to a highly expensive detection method. Also, there is a problem that the ratio of incorporation into a sample RNA or DNA is low and sufficient labeling of a sample RNA or DNA is impossible, resultantly, detection sensitivity is not sufficient. In contrast, fluorescence dye replacing Cy3 and Cy5 is not found to date.

An object of the present invention is to solve the above-mentioned problems and to provide a highly sensitive method of detecting a biological molecule at lower cost.

The present inventors have found that an organic EL (electroluminescence)-dye used in an organic EL element manifests high fluorescence intensity when used as a label of a biological molecule, in a process of searching for fluorescence dyes replacing Cy3 and Cy5, and achieved the present invention.

Namely, the method of detecting a biological molecule according to one embodiment of the present invention is characterized by that it includes reacting a biological molecule sample with an organic EL-dye and measuring the fluorescence of the biological molecule sample labeled with the organic EL-dye.

In the present invention, the biological molecule means a molecule species present in an organism, and includes those constituting the structure of an organism, those being concerned in production and conversion of energy, those ruling bioinformation, and the like. Specifically included are nucleic acids, proteins, saccharides, lipids, peptides, nucleotides, metabolic intermediates and metabolic enzymes, hormones, and neurotransmitters, and the like.

Between an organic EL-dye and a biological molecule, an amide bond, imide bond, urethane bond, ester bond, guanidine bond or thiourea bond can be formed. Prior to reaction with a biological molecule, any one reactive group selected from the group consisting of an isocyanate group, isothiocyanate group, epoxy group, halogenated alkyl group, triazine group, carbodiimide group and active ester carbonyl group can be introduced in the above-mentioned organic EL-dye. Further, any one selected from the group consisting of nucleic acids, proteins, peptides and saccharides can be used as the biological molecule sample.

The method of detecting a biological molecule according to another embodiment of the present invention is characterized by that it includes labeling of a biological molecule sample with a labeling dye comprising a 5-membered ring compound having a conjugate system and containing one or more hetero atom(s), selenium atom(s) or boron atom(s) and measurement of the fluorescence of the labeled biological molecule sample.

Also, a condensed poly-ring compound consisting of the above-mentioned 5-membered ring compound and a 6-membered ring compound having a conjugate system may be used. Further, an azole derivative or imidazole derivative can be used as the 5-membered ring compound. Prior to reaction with the above-mentioned biological molecule, any one reactive group selected from the group consisting of an isocyanate group, isothiocyanate group, epoxy group, halogenated alkyl group, triazine group, carbodiimide group and active ester carbonyl group can be introduced in an organic EL-dye.

The labeling dye according to another embodiment of the present invention is characterized by that it is a labeling dye used for detection of a biological molecule by measurement of fluorescence, wherein the dye includes an organic EL-dye having a reactive group to bind to a biological molecule. As the reactive group, any one functional group selected from the group consisting of a carboxyl group, isocyanate group, isothiocyanate group, epoxy group, halogenated alkyl group, triazine group, carbodiimide group and active ester carbonyl group can be used. As the organic EL-dye, a compound comprising a 5-membered ring compound having a conjugate system and containing one or more hetero atom(s), selenium atom(s) or boron atom(s) can be used. Further, a condensed poly-ring compound consisting of the above-mentioned 5-membered ring compound and a 6-membered ring compound having a conjugate system may also be used. Furthermore, an azole derivative or imidazole derivative may be used as the 5-membered ring compound.

The labeling kit for a biological molecule according to another embodiment of the present invention is characterized by that it includes an organic EL-dye for labeling a biological molecule. As the biological molecule, any one selected from the group consisting of nucleic acids, proteins, peptides and saccharides can be used. As the reactive group for the biological molecule, any one functional group selected from the group consisting of a carboxyl group, isocyanate group, isothiocyanate group, epoxy group, halogenated alkyl group, triazine group, carbodiimide group and active ester carbonyl group can be used. As the organic EL-dye, a compound comprising a 5-membered ring compound having a conjugate system and containing one or more hetero atom(s), selenium atom(s) or boron atom(s) can be used. Further, a condensed poly-ring compound consisting of the above-mentioned 5-membered ring compound and a 6-membered ring compound having a conjugate system may also be used. Furthermore, an azole derivative or imidazole derivative may be used as the 5-membered ring compound.

For example, when used as a kit of DNA microarray, a nucleic acid is used as the biological molecule sample and a probe nucleic acid is fixed on a microarray, while the target nucleic acid sample is labeled by reaction with an organic EL-dye, and the labeled target nucleic acid is spotted on the microarray and hybridization can be conducted under this conditions. Further, applying a binding property between avidin (streptavidin) and biotin, the avidin modified with this dye can be used as a biological assay kit for ELISA (enzyme-linked immunosorbent assay), Western blotting and the like. It can also be used as a kit for protein array. A cell can also be stained, due to efficient labeling of biological molecules such as saccharides and proteins.

According to the present invention, use of an organic EL-dye as a labeling dye for a biological molecule gives the following effects.

That is, an organic EL-dye shows high quantum yield in solid state (including solid state and semi-solid state) and manifests high fluorescence intensity. Since an organic EL-dye is cheap as compared with Cy3 and Cy5, a biological molecule can be detected at lower cost. Further, an organic EL-dye reacts with a biological molecule almost quantitatively and shows high incorporation ratio, therefore, high detection sensitivity can be obtained. Furthermore, use of said dye increases the degree of freedom of selectivity of fluorescence wavelength, and multiple fluorescence wavelengths of orange, yellow, green, blue and the like can be used. By this, it becomes possible to use two or more fluorescence dyes having large stokes shift (large difference between excited wavelength and fluorescence wavelength), consequently, plural target nucleic acids contained in one sample can also be simultaneously detected. While Cy3 and Cy5 need to be kept in refrigerated state, an organic EL-dye is chemically stable and can be kept for a long time at ambient temperature, therefore, handling thereof is easy.

BEST MODES FOR CARRYING OUT THE INVENTION

Figure 1A:
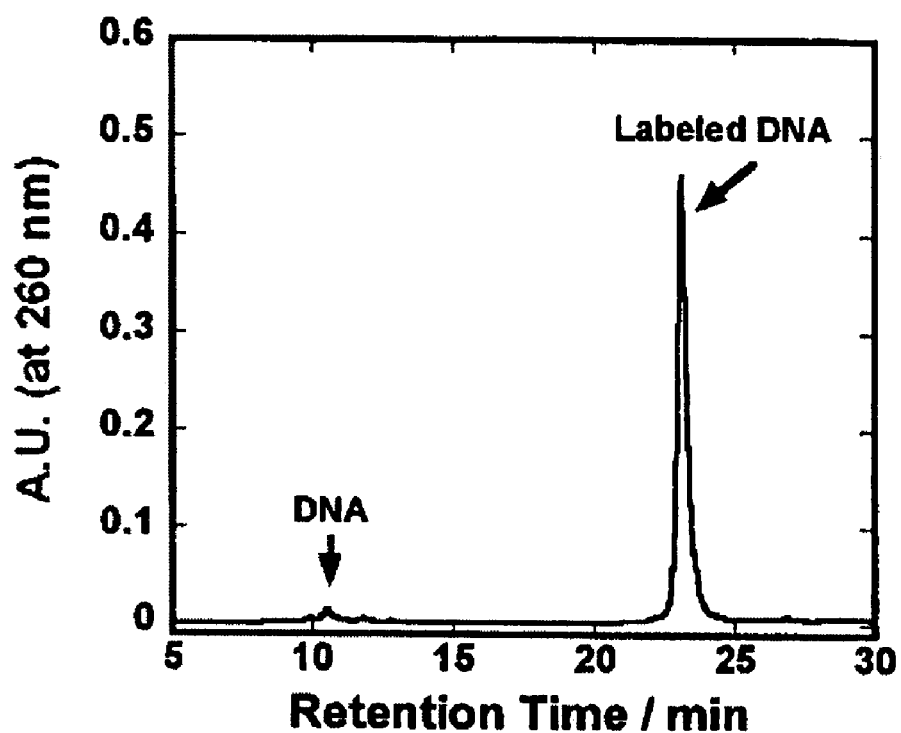
FIG. 1A shows one example of the HPLC profile of a labeled oligonucleotide in Example 1 of the present invention.

Hereafter, embodiments of the present invention will be explained in detail.

The organic EL-dye used in the present invention is not particularly limited provided it is a dye sandwiched in solid state between a pair of anode and cathode and capable of emitting by virtue of energy in recombination of a hole injected from an anode and an electron injected from a cathode. For example, poly-ring aromatic compounds such as tetraphenylbutadiene, perylene and the like, cyclopentadiene derivatives, distyrylpyrazine derivatives, acridone derivatives, quinacridone derivatives, stilbene derivatives, phenothiazine derivatives, pyradinopyridine derivatives, azole derivatives, imidazole derivatives, carbazole derivatives, tetraphenylthiophene derivatives and the like can be used. Further, a dye having a carboxyl group in the molecule or into which a carboxyl group can be introduced is preferable. The reason for this is that a reactive group for bonding with a biological molecule can be introduced easily as described below.

It is preferable that the organic EL-dye has a reactive group for bonding with a biological molecule sample (hereinafter, referred to target molecule) and the reactive group has a functional group capable of reacting with an amino group, imino group, thiol group, hydroxyl group, carboxyl group or aldehyde group of the target molecule. It is preferable that an amide bond, imide bond, urethane bond, ester bond, guanidine bond or thiourea bond is formed between an organic EL-dye and a biological molecule. As the functional group, for example, an isocyanate group, isothiocyanate group, epoxy group, halogenated sulfonyl group, acyl chloride group, halogenated alkyl group, glyoxal group, aldehyde group, triazine group, carbodiimide group and active ester carbonyl group and the like may be used. It is preferable that any one selected from the group consisting of an isocyanate group, isothiocyanate group, epoxy group, halogenated alkyl group, triazine group, carbodiimide group and active ester carbonyl group is used. The reason for this is that it can form an amide bond with an amino group in a target molecule and can directly bind to an imino group in a biological molecule. Further preferable is a triazine group, carbodiimide group or active ester carbonyl group. When these organic EL-dyes have a carboxyl group, an amino group and imino group present in a biological molecule can also be modified directly in the presence of a carbodiimide derivative and triazine derivative. Further, an organic EL-dye having a triazine group with an optional substituent or a carbodiimide group with an optional substituent can react directly with an imino group of guanine and thymine in DNA bases, therefore, introduction of a dye by a PCR (polymerase chain reaction) method is not necessary, and application thereof to mismatch detection and the like is possible.

For example, as the active ester carbonyl group, N-hydroxysuccinimide ester and maleimide ester can be used. By use of N-hydroxysuccinimide, an EL-dye and a target molecule can be bound by an amide bond via an N-hydroxysuccinimide ester using N,N'-dicyclohexylcarbodiimide (DCC) as a condensing agent, as shown in formula I in the following Scheme 1. Further, as shown in formula II in the Scheme 1, a triazine derivative can also be used as the active ester carbonyl group. As the carbodiimide group, carbodiimide reagents such as DCC and 1-cyclohexyl-3-(2-morpholinoethyl)carbodiimide and the like can be used. An EL-dye and a target molecule can be bound by an amide bond via a carbodiimide (formula III). Further, an EL-dye having previously a carbodiimide group or triazine group in the molecule can also be bound directly to an amino group and imino group in a biological molecule (formula IV).

Furthermore, excitation wavelength and emission wavelength can be changed by changing a substituent on an organic EL-dye, therefore, a plurality of samples can also be simultaneously detected by virtue of a plurality of colors.

Scheme 1

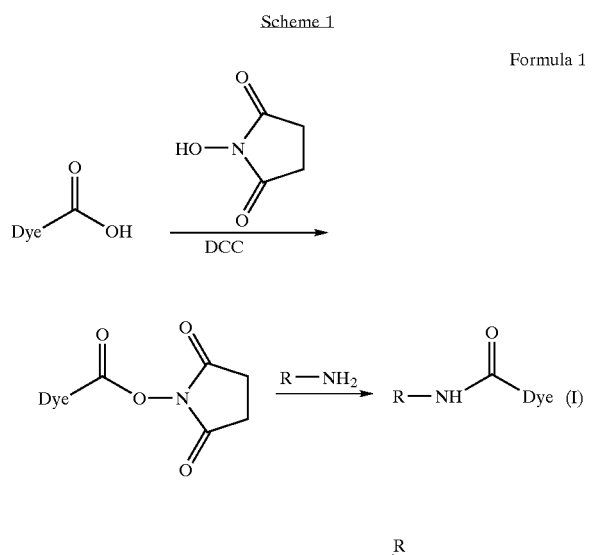

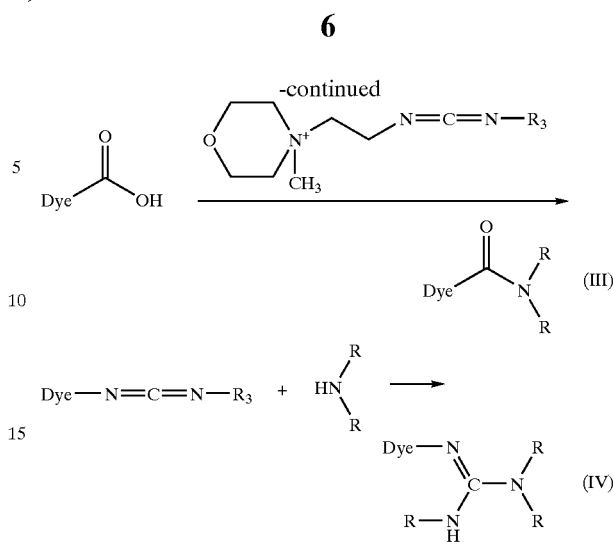

A reactive group can be bound with an amino residue modified at the end of oligo DNA when the target molecule is DNA, with amino residue in the case of a protein, an amino group of a polypeptide, for example, an amino residue of a polylysine derivative in the case of peptides, and with an amino group in a polysaccharide derivative skeleton in the case of a polysaccharide.

As the preferable organic EL-dye used in the detection method of the present invention, the compounds being comprised of a 5-membered ring compound having a conjugate system and containing one or more hetero atom(s), selenium atom(s) or boron atom(s) are given. Further specifically, a mono-ring compound composed of a 5-membered ring compound having a conjugate system, and a condensed poly-ring compounds consisting of 6-membered ring compound having a conjugate system and the 5-membered ring compound are given. The reason for this is that they have large quantum yield and show intense fluorescence even in solid state.

Specific examples of the condensed poly-ring compound are explained below.

Formula 2

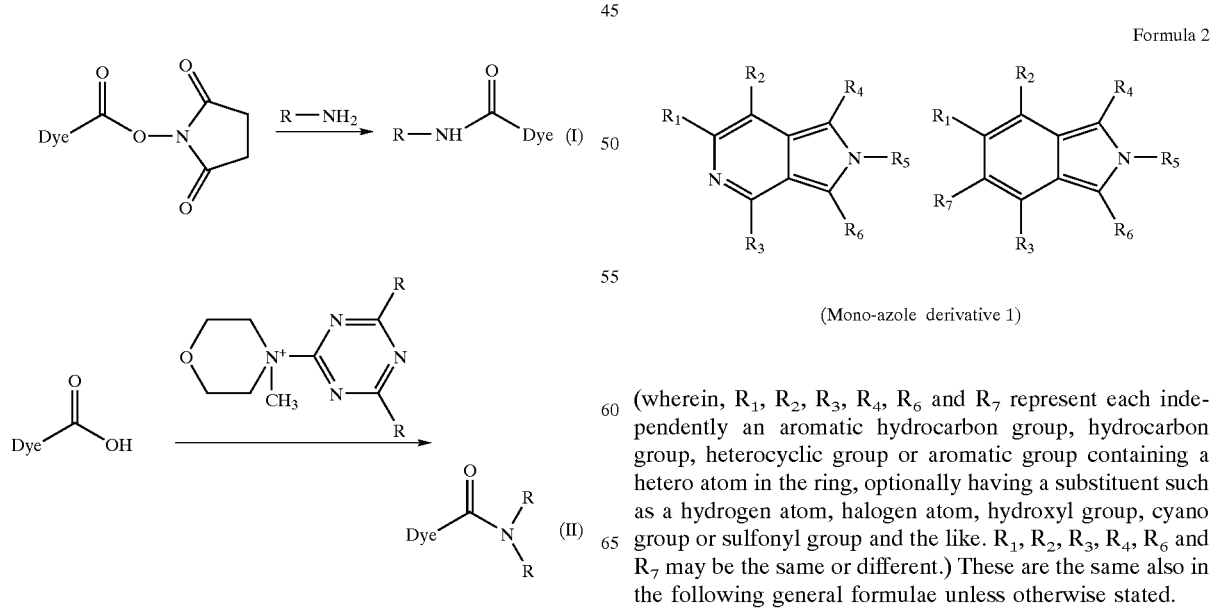

(Mono-azole derivative 1)

(wherein, $R_1$, $R_2$, $R_3$, $R_4$, $R_6$ and $R_7$ represent each independently an aromatic hydrocarbon group, hydrocarbon group, heterocyclic group or aromatic group containing a hetero atom in the ring, optionally having a substituent such as a hydrogen atom, halogen atom, hydroxyl group, cyano group or sulfonyl group and the like. $R_1$, $R_2$, $R_3$, $R_4$, $R_6$ and $R_7$ may be the same or different.) These are the same also in the following general formulae unless otherwise stated.

Formula 3

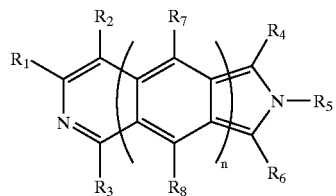

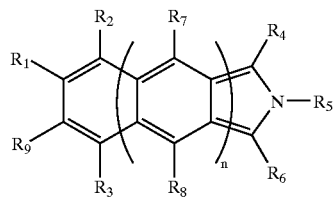

(Mono-azole derivative2)

(wherein, $R_8$ and $R_9$ represent each an aromatic hydrocarbon group, hydrocarbon group, heterocyclic group or aromatic group containing a hetero atom in the ring, optionally having a substituent such as a hydrogen atom, halogen atom, hydroxyl group, cyano group or sulfonyl group and the like. $R_8$ and $R_9$ may be the same or different.) These are the same also in the following general formulae unless otherwise stated. (wherein, n represents an integer of 1 or more, preferably of 1 to 5.) This is the same also in the following general formulae.

Formula 4

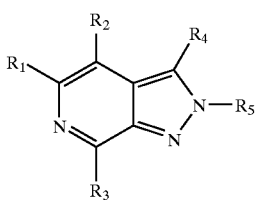

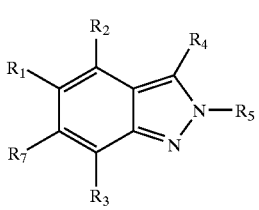

(Diazole derivative 1)

Formula 5

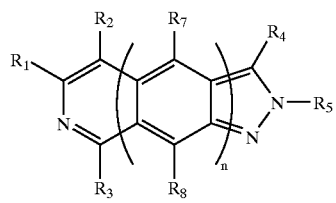

-continued

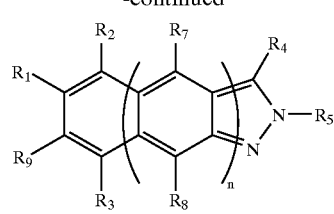

(Diazole derivative 2)

Formula 6

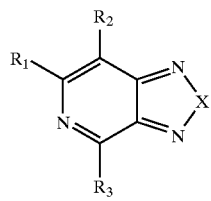

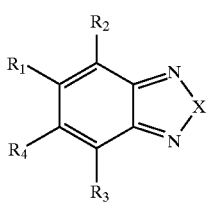

(Diazole derivative 3)

(wherein, $R_1$, $R_2$, $R_3$ and $R_4$ represent each independently an aromatic hydrocarbon group, hydrocarbon group, heterocyclic group or aromatic group containing a hetero atom in the ring, optionally having a substituent such as a hydrogen atom, halogen atom, hydroxyl group, cyano group or sulfonyl group and the like. $R_1$, $R_2$, $R_3$, $R_4$, $R_6$ and $R_7$ may be the same or different. As $R_2$ and $R_3$, aromatic hydrocarbon groups optionally having a substituent are preferable, and as this substituent, alkyl groups and alkoxy groups having 1 to 4 carbon atoms, or a bromine atom are preferable. Further, as the alkyl group, a methyl group, and as the alkoxy group, a methoxy group, are preferably used, respectively. X represents a nitrogen atom, sulfur atom, oxygen atom, selenium atom or boron atom, optionally having a substituent.) This is the same also in the following general formulae unless otherwise stated.

Formula 7

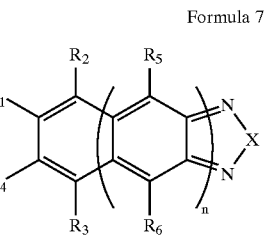

(Diazole derivative 4)

Formula 8

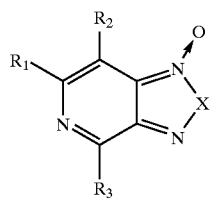 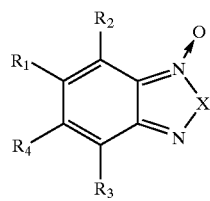

(Diazole derivative 5)

(wherein, N→O represents a state in which a nitrogen atom is coordinate-bonded to an oxygen atom.)

Formula 9

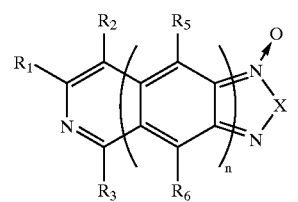 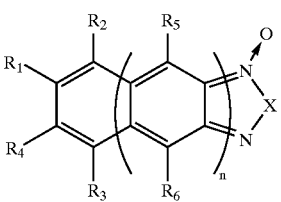

(Diazole derivative 6)

Formula 10

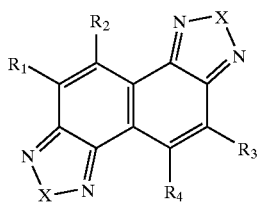

(Diazole derivative 7)

Formula 11-1

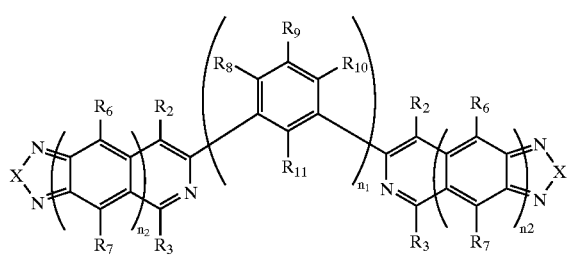

(Diazole derivative 8)

Formula 11-2

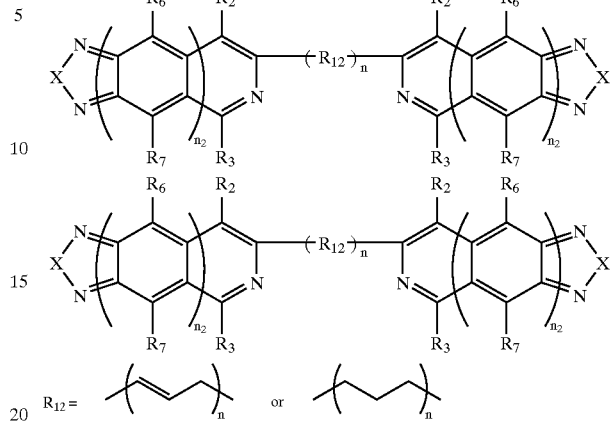

$R_{12} =$ 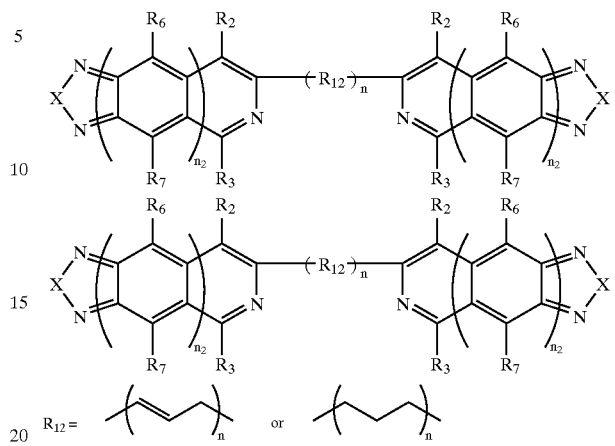

(wherein, $R_{10}$ and $R_{11}$ represent each an aromatic hydrocarbon group, hydrocarbon group, heterocyclic group or aromatic group containing a hetero atom in the ring, optionally having a substituent such as a hydrogen atom, halogen atom, hydroxyl group, cyano group or sulfonyl group and the like. $R_{10}$ and $R_{11}$ may be the same or different. $R_{12}$ is an olefin group or paraffin group optionally having a substituent, and n represents an integer of 1 to 3, preferably 1.) These are the same in the following formulae unless otherwise stated.

Formula 12-1

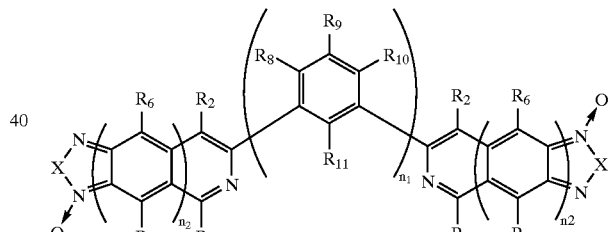

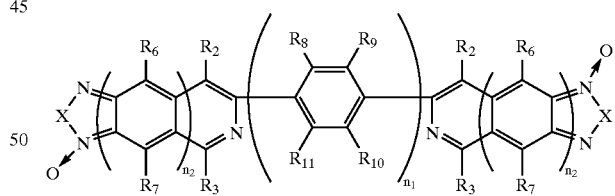

(Diazole derivative 9)

Formula 12-2

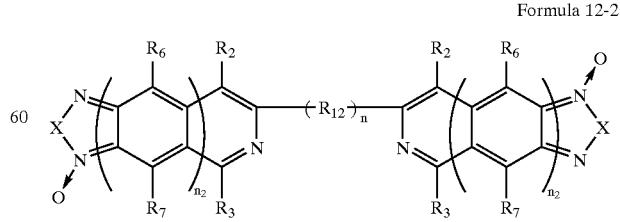

-continued

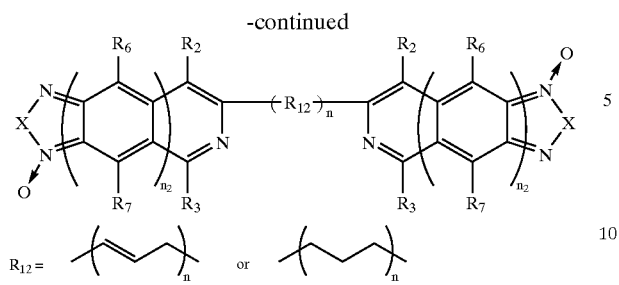

The above-mentioned diazole derivatives are not particularly limited, but an oxadiazolopyridine derivative of the following general formula can be suitably used.

Formula 13

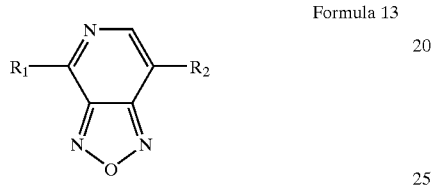

Regarding the oxazolopyridine derivative, its carboxylic acid derivative is synthesized, then, it is derived into an active ester containing N-hydroxysuccinimide ester using N,N'-dicyclohexylcarbodiimide (DCC) as a condensing agent, for example, according to a reaction shown in the following Scheme 2, and the resulting derivative is used.

Scheme 2

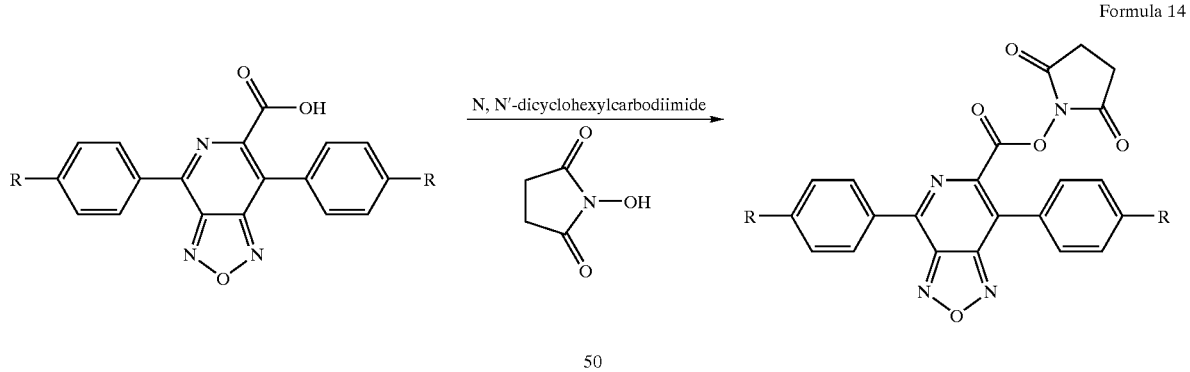

Formula 14

Formula 15

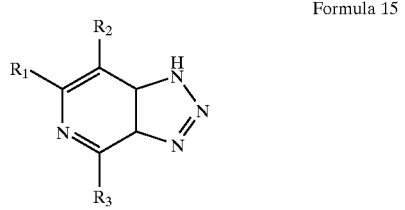

(Triazole derivative 1)

Formula 16

(Triazole derivative 2)

As the 5-membered ring compound, the following derivatives containing a thiophene group can also be used.

Formula 17

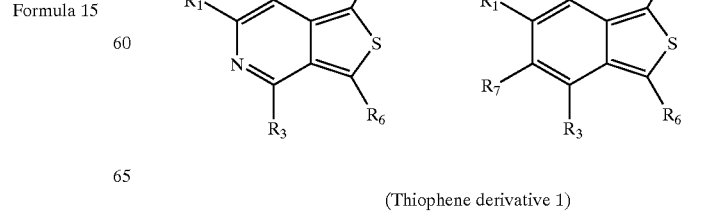

(Thiophene derivative 1)

-continued

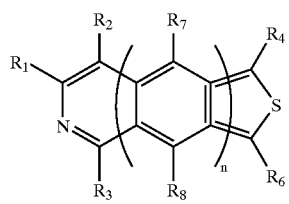

(Triophene derivative 2) Formula 18

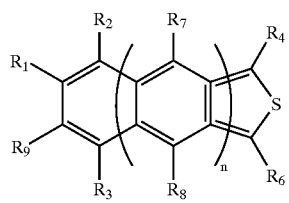

(Thiophene derivative 3)

In the case of a thiophene derivative, a 2,3,4,5-tetraphenylthiophene derivative which is a non-condensed type compound and represented by the following general formula can also be used.

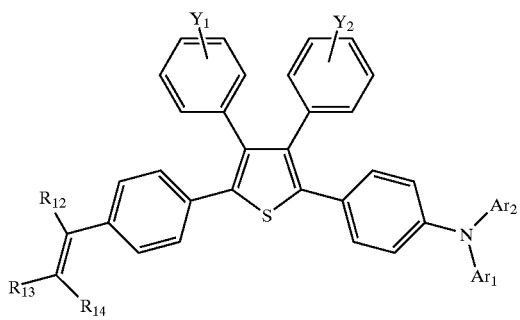

Formula 19

(wherein, $R_{12}$, $R_{13}$ and $R_{14}$ represent each independently a hydrogen atom, linear-, branched- or cyclic-alkyl group, substituted or unsubstituted aryl group, or substituted or unsubstituted aralkyl group, $Ar_1$ and $Ar_2$ represent a substituted or unsubstituted aryl group, further, $Ar_1$ and $Ar_2$ may form a nitrogen-containing heterocyclic ring together with a bonded nitrogen atom. $Y_1$ and $Y_2$ represent a hydrogen atom, halogen atom, linear-, branched- or cyclic-alkyl group, linear-, branched- or cyclic-alkoxy group, substituted or unsubstituted aryl group, substituted or unsubstituted aralkyl group, or substituted or unsubstituted amino group.)

(Thiophene Derivative 4)

A 2,3,4,5-tetraphenylthiophene derivative of the following general formula can also be used.

Formula 20

[Formula structure]

(wherein, $Ar_1$ to $Ar_6$ represent each independently a substituted or unsubststituted aryl group, further, $Ar_1$ and $Ar_2$, $Ar_3$ and $Ar_4$, and $Ar_5$ and $Ar_6$ may form a nitrogen-containing heterocyclic ring together with a bonded nitrogen atom.)

Further, an imidazole can also be used as the 5-membered ring compound, for example, imidazole derivatives of the following general formulae.

Formula 21

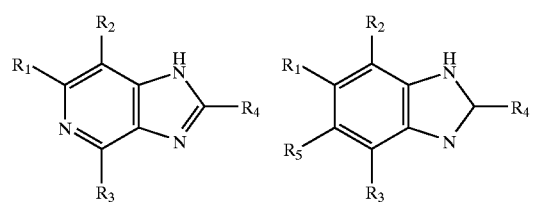

(Imidazole derivative 1)

-continued
Formula 22
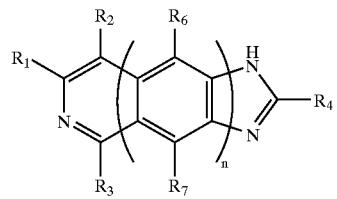
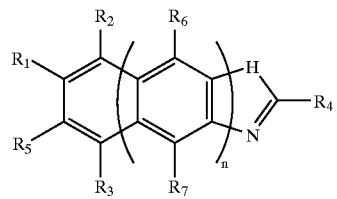
(Imidazole derivative 2)
Formula 23-1
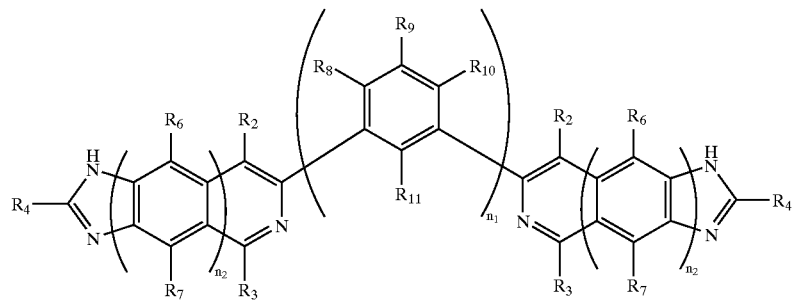
$n_1 = 1-5, \; n_2 = 0-5$
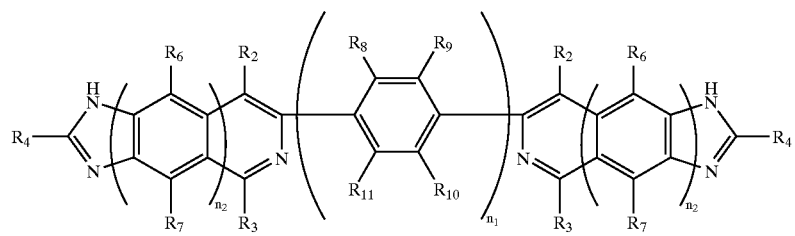
$n_1 = 1-5, \; n_2 = 0-5$
(Imidazole derivative 3)
Formula 23-2
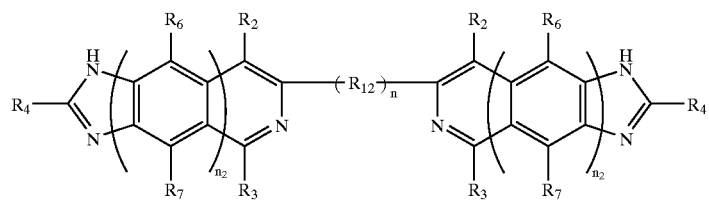
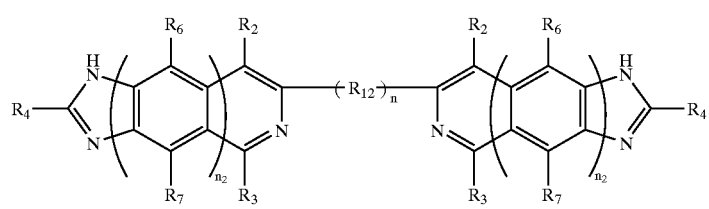

-continued

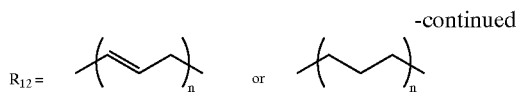

(wherein, in the imidazole skeleton, a plurality of units may be bonded to any position of center benzene rings $R_8$, $R_9$, $R_{10}$ and $R_{11}$. $R_{12}$ is an olefin group or paraffin group optionally having a substituent, and n represents an integer of 1 to 3, preferably 1.).

(Carbazole Derivative)

A carbazole derivative of the following general formula can also be used.

Formula 24

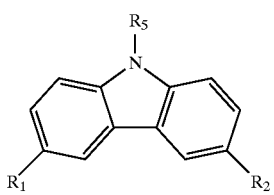

Further, a 5-membered ring compound which is a mono-ring compound having a conjugate system and containing one or more hetero atom(s), selenium atom(s) or boron atom(s) can also be used. Though not particularly limited, azole derivatives of the following general formula, for example, can also be used.

Formula 25

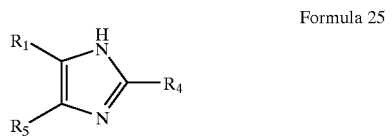

(wherein, $R_1$, $R_4$ and $R_5$ represent each independently an aromatic hydrocarbon group, hydrocarbon group, heterocyclic group or aromatic group containing a hetero atom in the ring, optionally having a substituent such as a hydrogen atom, halogen atom, hydroxyl group, cyano group or sulfonyl group and the like. $R_1$, $R_4$ and $R_5$ may be the same or different.)

The detection method of the present invention can be applied to any detection method provided it is a method of measuring the fluorescence of a labeled biological molecule in solid or semi-solid state. For example, when used for gene analysis using a DNA microarray, it can be conducted according to the following procedure.

In the case of investigation of a gene expression, those prepared by amplifying cDNA and the like by a PCR method using a cDNA library, genome library or whole genome as a template can be used as the probe nucleic acid to be fixed on a substrate. In the case of investigating of a gene mutation and the like, various oligonucleotides corresponding to the mutation and the like synthesized based on a known sequence as a standard can be used.

Fixation of a probe nucleic acid onto a substrate can be conducted by a suitable method selected depending on the kind of a nucleic acid and the kind of a substrate. For example, a method can also be used in which a probe nucleic acid is electrostatically-bonded to a substrate surface-treated with a cation of polylysine and the like by use of the charge of DNA.

On the other hand, a labeled target nucleic acid with an organic EL-dye is prepared by mixing a target nucleic acid and an organic EL-dye and reacting together. The reaction temperature is preferably from room temperature to 60° C. and the reaction time is preferably from 2 to 48 hours.

Then, the labeled target nucleic acid is spotted on a substrate, and hybridization thereof is conducted. Hybridization is preferably conducted at from room temperature to 70° C. for 2 to 48 hours. By hybridization, a target nucleic acid having a base sequence complimentary to a probe nucleic acid is selectively bonded to a probe nucleic acid. Thereafter, the substrate is washed and dried at room temperature.

Then, the fluorescence intensity of the surface of the dried substrate is measured by a fluorescence laser scanner method. By fluorescence intensity, the level of gene expression can be monitored.

Regarding the above-mentioned hybridization, a method of fixing a probe nucleic acid onto a substrate has been explained, however, a method can also be used in which a target nucleic acid labeled previously with an organic EL-dye is fixed on a substrate and a probe nucleic acid is spotted on a substrate.

The labeling kit of the present invention contains an organic EL-dye or derivative thereof for labeling a biological molecule, and if necessary, it can contain reagents, enzymes, solvents and the like, for reacting a dye with the object biological molecule. The object biological molecules include a nucleic acid, protein, peptide or saccharide. The organic EL-dye is preferably a derivative having a functional group reacting with an amino group of a biological molecule. Examples of the functional group preferably include any one selected from an isocyanate group, isothiocyanate group, epoxy group, halogenated alkyl group, triazine group, carbodiimide group and active ester carbonyl group. Further preferably, an active ester containing a triazine group, carbodiimide group or active ester carbonyl group is contained as a derivative of an organic EL-dye.

The present invention will be further specifically explained in more detail in the following examples.

SYNTHESIS EXAMPLE 1

A 1,2,5-oxadiazolo-[3,4-c]pyridine derivative was used as the organic EL-dye.

The scheme for synthesis of an active ester of a 1,2,5-oxadiazolo-[3,4-c]pyridine (hereinafter, abbreviated as EL-OSu) will be shown below.

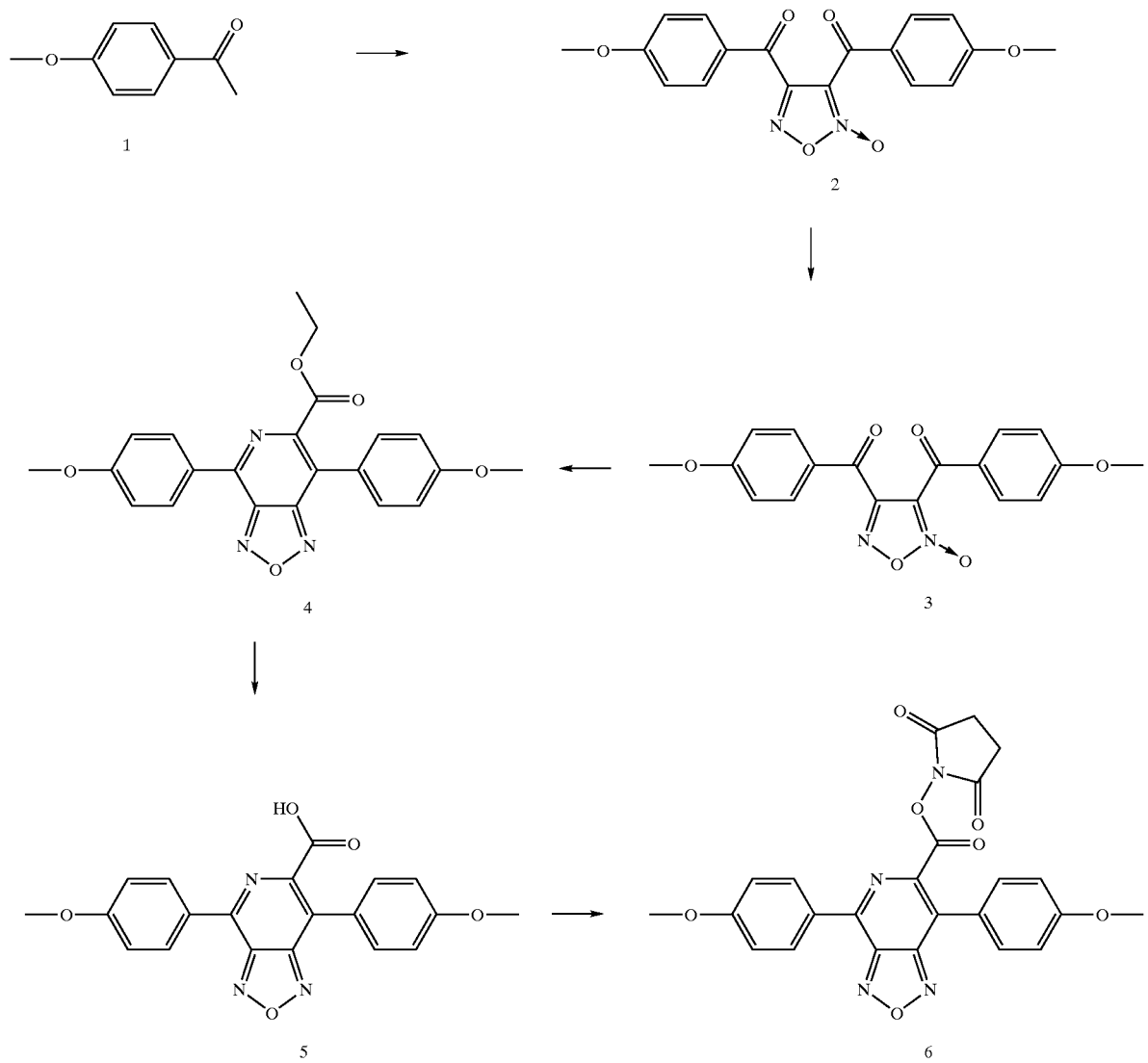

Scheme 3

(1) Synthesis of Diketone Derivative (2)

In a 500 mL three-necked flask, 37.5 g (0.25 mol) of 4-methoxyacetophenone (1) and 0.15 g of sodium nitrite were dissolved in 100 mL of acetic acid. On a water bath, a solution prepared by dissolving 100 mL of $HNO_3$ in 100 mL of acetic acid was added dropwise over 2 hours. Then, the mixture was stirred at room temperature for 2 days. The reaction mixture was slowly added into 500 mL of water to cause precipitation. The precipitate was filtrated and dissolved in chloroform. The chloroform phase was washed with saturated sodium bicarbonate water, and washed twice with a 10% NaCl aqueous solution. After dehydration over $MgSO_4$, chloroform was distilled off under reduced pressure to obtain 34.5 g (yield: 78%) of oxadiazole-N-oxide (2).

(2) Synthesis of Diketone Derivative (3)

In a 500 mL three-necked flask, 17.7 g (0.05 mol) of oxadiazole-N-oxide (2) was dissolved in 400 mL of acetonitrile. Into this was added 12.0 g of Zn, 7 mL of AcOH and 20 mL of $Ac_2O$. On a water bath, the resulted mixture was cooled so that the reaction temperature did not exceed 30° C. The mixture was stirred for 12 hours to terminate the reaction. The reaction mixture was filtrated to remove insoluble materials. Acetonitrile was distilled off under reduced pressure to obtain a residue. The residue was recrystallized from chloroform to obtain 10.2 g (yield: 60%) of oxadiazole-N-oxide (3).

(3) Synthesis of Oxadiazolopyridine Ethyl Ester (4)

In a 500 mL three-necked flask, 15.6 g (0.046 mol) of oxadiazole-N-oxide (3) was dissolved in 300 mL of butanol. Into this was added 32.0 g (0.23 mol) of a glycine ethyl ester hydrochloride. The mixture was heated to reflux for 24 hours Butanol was distilled off under reduced pressure to obtain a residue. The residue was dissolved in 200 mL of chloroform, and washed with 10% HCl, saturated $NaHCO_3$ and 10% NaCl. This was dried over $MgSO_4$ and the solvent was distilled off. The resulted residue was recrystallized from chloroform to obtain 13.0 g (yield: 70%) of oxadiazolopyridine ethyl ester (4).

(4) Hydrolysis of Oxadiazolopyridine Ethyl Ester (4)

In a 500 mL three-necked flask, 3.0 g (0.007 mol) of oxadiazolopyridine ethyl ester (4) was dissolved in 200 mL of ethanol. To this was added 0.62 g (0.01 mol) of KOH. After heating to reflux for 5 hours, the reaction mixture was added to 200 mL of water. Into this aqueous solution, concentrated hydrochloric acid was added dropwise to adjust pH to 1 toobtain a precipitate. The precipitate was filtrated and dissolved in chloroform. The chloroform phase was washed with a 10% $NaHCO_3$ aqueous solution and water. Chloroform was distilled off to obtain a residue. The residue was recrystallized from water-ethanol (1:1) to obtain 2.1 g (yield: 81%) of oxadiazolopyridinecarboxylic acid (5)

Synthesis of Active Ester (6)

In a 50 mL three-necked flask, 1.0 g (0.0026 mol) of oxadiazolopyridinecarboxylic acid (5) and 0.30 g (0.0026 mol) of N-hydroxysuccinimide were dissolved in 20 mL of DMF. Into this, 0.54 g (0.0026 mol) of N,N'-dicyclohexylcarbodiimide was added dropwise over 30 minutes. After dropping, the mixture was stirred for 30 hours at room temperature. Under reduced pressure, DMF was distilled off. The residue was isolated and purified by silica gel column chromatography (chloroform) to obtain 0.76 g (yield: 62%) of an oxadiazolopyridine active ester (6).

SYNTHESIS EXAMPLE 2

An imidazolopyridine ethyl ester derivative was used as a organic EL-dye. The scheme for synthesis of an active ester of a imidazolopyridine ethyl ester (hereinafter, abbreviated as im-EL-OSu) will be shown below.

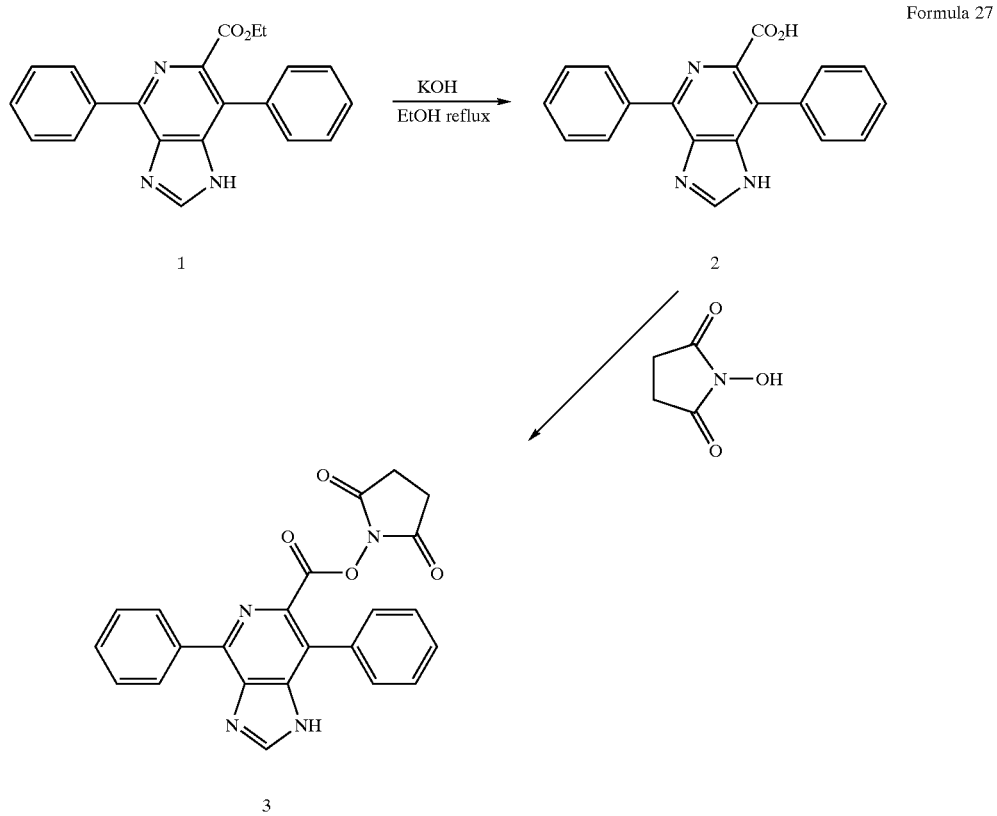

Scheme 4

Formula 27

(1) Hydrolysis of Imidazolopyridine Ethyl Ester (1)

In a 500 mL three-necked flask, 0.5 g (1.5 mmol) of an ester 1 was dissolved in 50 mL of ethanol. To this was added 0.12 g (2.1 mol) of KOH. After heating to reflux for 5 hours, the reaction mixture was added to 50 mL of water. Into this aqueous solution, concentrated hydrochloric acid was added dropwise to adjust pH to 1 to obtain a precipitate. The precipitate was filtrated and dissolved in chloroform. The chloroform phase was washed with a 10% $NaHCO_3$ aqueous solution and water. Chloroform was distilled off to obtain a residue. The residue was recrystallized from water to obtain 0.3 g (yield: 63%) of a carboxylic acid 2.

(2) Synthesis of Active Ester (3)

In a 50 mL three-necked flask, 0.2 g (0.6 mmol) of a carboxylic acid derivative 2 and 0.07 g (0.6 mmol) of N-hydroxysuccinimide were dissolved in 10 mL of DMF. Into this, 0.12 g (0.6 mmol) of N,N'-dicyclohexylcarbodiimide was added dropwise over 30 minutes. After dropping, the mixture was stirred for 30 hours at room temperature. Under reduced pressure, DMF was distilled off. The residue was isolated and purified by silica gel column chromatography (chloroform) to obtain 0.14 g (yield: 55%) of an active ester 3.

EXAMPLE 1

<Labeling of Oligonucleotide with Dye, and Detection Thereof (1)>

1. Labeling of Oligonucleotide with Dye

Labeling of an oligonucleotide with a dye was conducted according to the following Scheme 4.

Scheme 4.

Formula 28

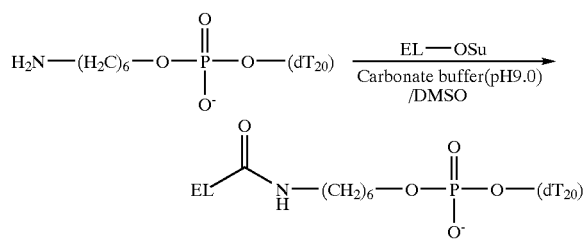

(Experimental Procedure)

Into 40 µl of Na2CO$_3$/NaHCO$_3$ buffer (pH 9.0) containing H$_2$N-dT$_2$O (40 mmol) was added 12 µl of an anhydrous DMSO solution containing 5.0 µmol (2.4 mg) of an active ester of an organic EL-dye and the mixture was shaken at room temperature for 6 hours. After shaking, 0.1 M TEAA (triethylamine acetic acid) buffer (pH 7.0) was added so as to give the total volume of 1 ml, and components derived from the oligonucleotide were separated using NAP-10 column (Pharmacia Sephadex G-25). In this operation, the NAP-10 column had been equilibrated previously with 15 ml of 0.1 M TEAA buffer before use. The sample solution of which total volume had been adjusted to 1 ml was applied into in a column. After elution of 1 ml of the solution, 0.1 M TEAA buffer was charged in a volume of 1.5 ml. Immediately after this, 1.5 ml of the eluted solution was separated. The resulted solution was freeze-dried over night, and 20 µl of sterile distilled water was added and analyzed by reverse phase HPLC. The solution injected into HPLC was previously diluted to 1/40 and analyzed.

(HPLC Measurement Conditions)

Column: Lichrospher RP-18 (Cica-MERCK)
Flow rate: 1 ml/min
Detection wavelength: 260 nm
Sample injection solvent: ultra-pure water
Eluent A: 0.1 M TEAA buffer (pH 7.0), 10% CH$_3$CN solution
Eluent B: 0.1 M TEAA buffer (pH 7.0), 40% CH$_3$CN solution

TABLE 1

Gradient conditions of HPLC measurement

|   | 0 | 30 | 35 | 40 (min) |
|---|---|----|----|----------|
| A | 100 | 0 | 0 | 100 (%) |
| B | 0 | 100 | 100 | 0 (%) |

Figure 1B:
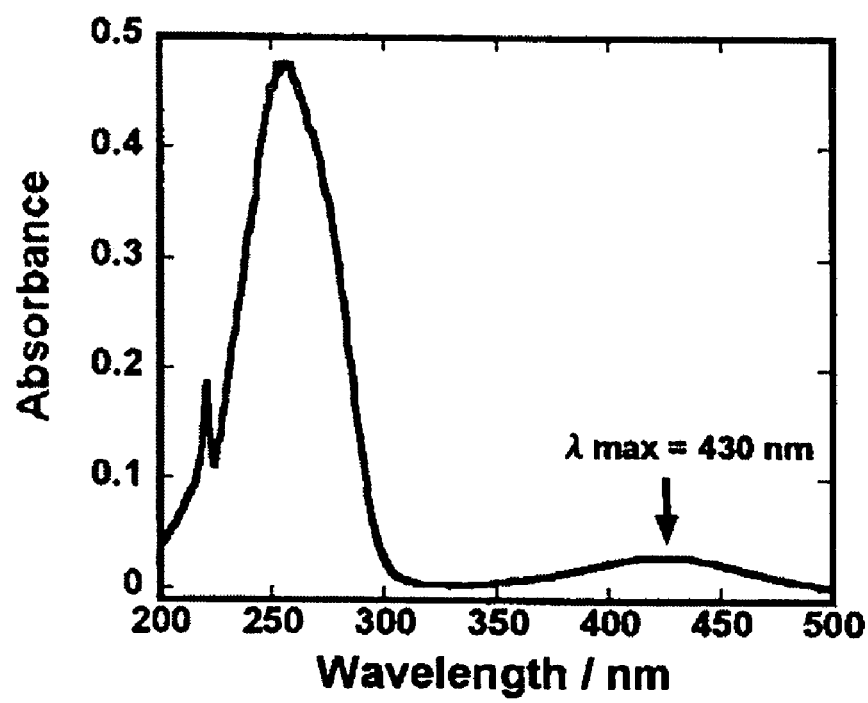
FIG. 1B shows one example of the UV spectrum of an intended labeled oligonucleotide in Example 1 of the present invention.
Figure 2:
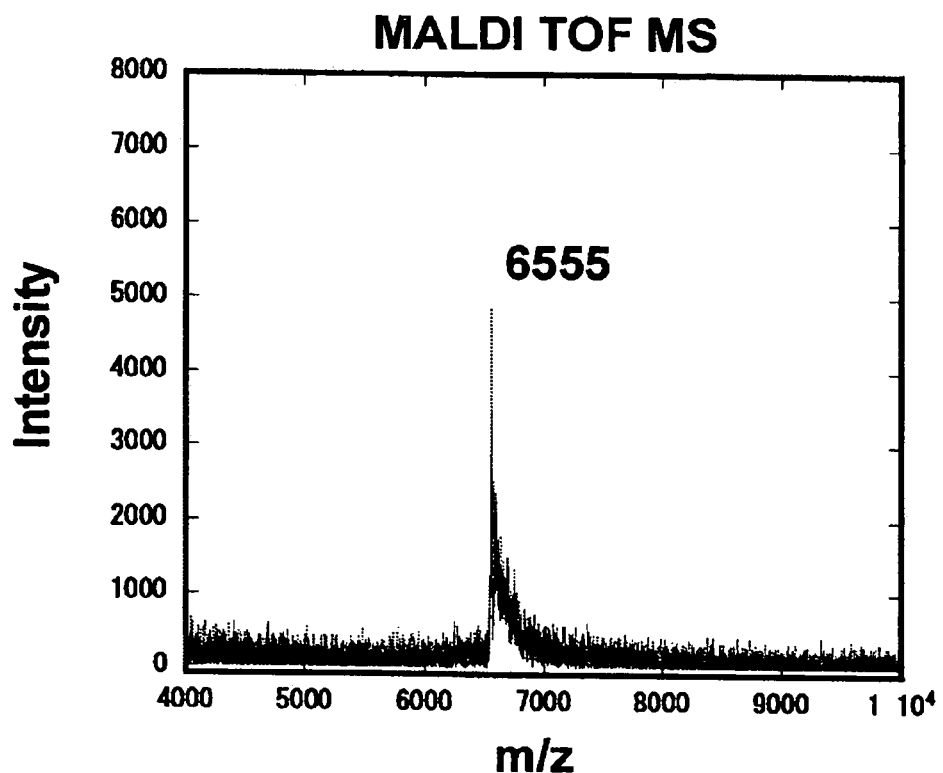
FIG. 2 shows one example of the TOF MS spectrum of a labeled oligonucleotide in Example 1 of the present invention.
Figure 3:
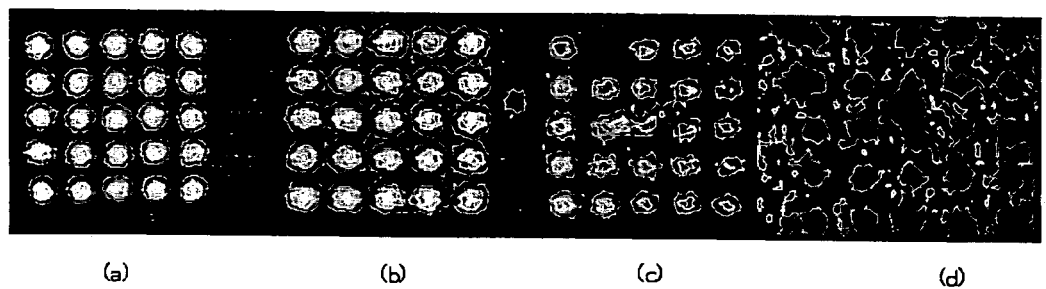
FIG. 3 shows one example of the emission pattern of a labeled oligonucleotide in Example 1 of the present invention, and (a), (b), (c) and (d) show results of 110 fmol, 10 fmol, 1 fmol and 0.5 fmol, respectively.

The HPLC profile of the labeled oligonucleotide and the UV spectrum of the intended material are shown in FIG. 1A and FIG. 1B, respectively. As a result of HPLC, a peak around RT=30 min was confirmed to be the intended material, and preparative HPLC was conducted. Identification of the resulted intended material was conducted by MALDI (Matrix Assisted Laser Desorption/Ionization) TOF MS. The result is shown in FIG. 2. The reaction ratio was calculated from the peak area in HPLC chromatogram to find a ratio of about 90%, namely, the active ester (6) of an EL-dye was reacted almost quantitatively with oligo DNA.

2. Detection of Labeled Oligonucleotide

Next, solutions of different concentration of the labeled oligonucleotide were prepared as shown in the following Table 2. Then, 1 nL of the solution was spotted on a glass substrate (5×5). After spotting, the glass substrate was dried.

TABLE 2

| Solution concentration (µM) | Relative concentration of labeled oligonucleotide (fmol) |
|---|---|
| 110 | 110 |
| 11 | 11 |
| 1 | 1 |
| 0.5 | 0.5 |

Next, the detection limit thereof was investigated by a fluorescence scanner. The results are shown in Table 3. Here, (a), (b), (c) and (d) show results of 110 fmol, 10 fmol, 1 fmol and 0.5 fmol, respectively.

Here, as the detection instrument, BIO-RAD molecule imager FX Pro was used. The laser wavelength was 488 nm and the scan interval was 50 nm.

(Result)

The excitation light used in this detection is laser light of 488 nm and the excitation wavelength of the fluorescence dye is 438 nm. Irrespective of this, the detection limit of the relative concentration of the labeled oligonucleotide was 0.5 fmol (500 amol), and therefore, detection in high sensitivity was possible. The reaction with DNA was almost quantitative, and the reaction time could be reduced from conventional times of about 24 hours to about 6 hours. Further, this EL-dye was stable, and even when re-measurement was conducted using an EL-dye preserved at room temperature for 15 days, the equivalent results were obtained.

EXAMPLE 2

<Labeling of Oligonucleotide with Dye, and Detection Thereof (2)>

1. Labeling of Oligonucleotide with Dye

Labeling of an oligonucleotide with a dye was conducted according to the following Scheme 4. The labeling conditions are the same as that for Example 1. The addition reaction of an imidazole derivative progressed quickly and almost quantitatively.

Scheme 5.

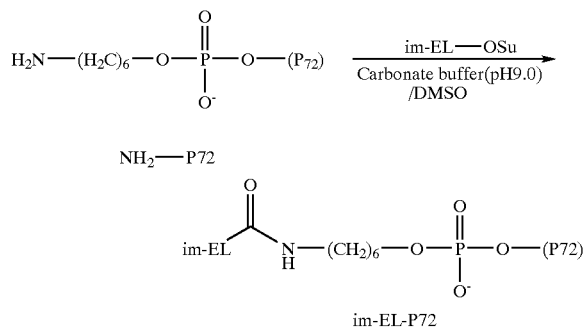

Formula 29

Figure 4A:
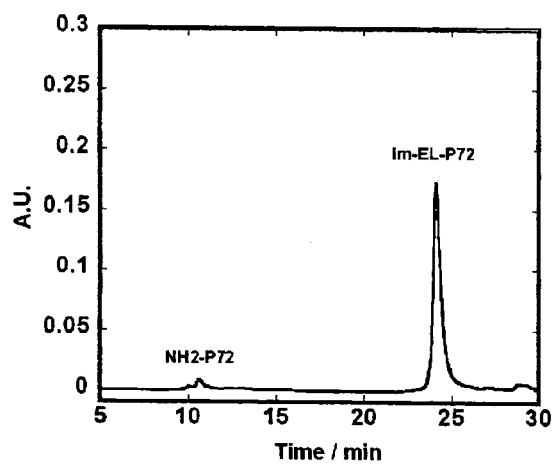
FIG. 4A shows one example of the HPLC profile of a labeled oligonucleotide in Example 2 of the present invention.
Figure 4B:
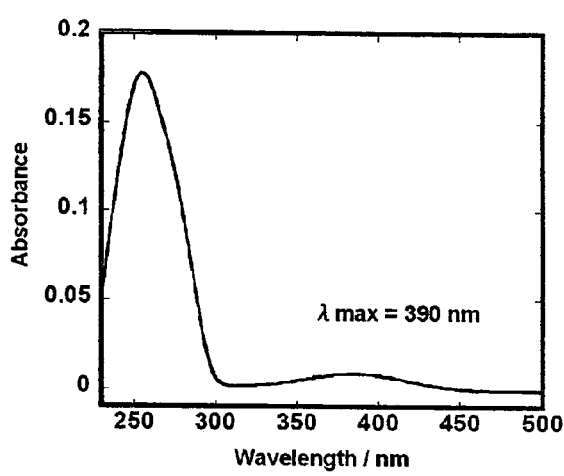
FIG. 4B shows one example of the UV spectrum of an intended labeled oligonucleotide in Example 2 of the present invention.

(HPLC Measurement Conditions)
Column: Lichrospher RP-18 (Cica-MERCK)
Flow rate: 1 ml/min
Detection wavelength: 260 nm
Sample injection solvent: ultra-pure water
Eluent A: 0.1 M TEAA buffer (pH 7.0), 10% $CH_3CN$ solution
Eluent B: 0.1 M TEAA buffer (pH 7.0), 40% $CH_3CN$ solution The gradient conditions of HPLC measurement are the same as that of Example 1. The HPLC profile of the labeled oligonucleotide and the UV spectrum of the intended material are shown in FIG. 4A and FIG. 4B, respectively. As a result of HPLC, a peak around RT=25 min was confirmed to be the intended material, and preparative HPLC was conducted.

Figure 5:
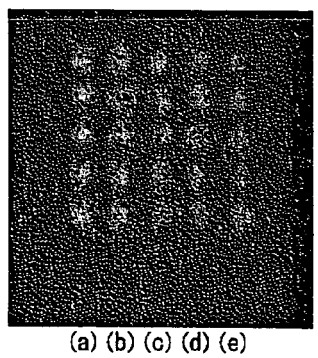
FIG. 5 shows one example of the emission pattern of a labeled oligonucleotide in Example 2 of the present invention, and (a), (b), (c), (d) and (e) show results of 500 fmol, 250 fmol, 100 fmol, 50 fmol and 10 fmol, respectively.

Next, the detection limit thereof was investigated by fluorescence scanner in the same manner as that of the example. The results are shown in FIG. 5. Here, (a), (b), (c), (d) and (e) show emission patterns of 500 fmol, 250 fmol, 100 fmol, 50 fmol and 10 fmol, respectively.

(Result)
The detection limit of the relative concentration of the labeled oligonucleotide was 10 fmol, and therefore, detection in high sensitivity was possible. The reaction of the oligonucleotide and EL-dye was almost quantitative.

EXAMPLE 3

<Labeling and Detection of Peptides>

1. Synthesis of Ac-Lys(EL)-Lys-Lys-Lys(Acr)-Lys-Lys-Lys(Acr)-Lys-Lys-$NH_2$ (1) Synthesis of Ac-Lys(Mtt)-(Lys(Boc))$_2$-Lys-(Acr)-(Lys(Boc))$_2$-Lys(Acr)-(Lys(Boc))$_2$-Resin (where, Lys denotes lysine, Mtt denotes 4-methyltrityl, Boc denotes tert-butyloxycarbonyl, and Acr Denotes Acridinyl, Respectively)

(Experimental Procedure)
Into a reaction vessel, 0.15 g (0.61 mmol/g) of Fmoc (9-fluorenylmethyloxycarbonyl)-NH-SAL (super acid labile) Resin was charged, and 0.26 g of Fmoc-Lys(Acr)-OH was added in each of cartridges 3, 6, 0.18 g of Fmoc-Lys(Boc)-OH was added in each of cartridges 1, 2, 4, 5, 7 and 8, and 0.23 g of Fmoc-Lys(Mtt)-OH was added in a cartridges 9. Subsequently, synthesis was conducted using 431A peptide synthesizer of Applied Biosystems. The standard Fmoc method was followed, and the N-terminal was acetylated. A yellow solid peptide resin was obtained. The yield was 0.30 g.

(2) Deprotection of Mtt Group of Ac-Lys(Mtt)-(Lys(Boc))$_2$-Lys-(Acr)-(Lys(Boc))$_2$-Lys(Acr)-(Lys(Boc))$_2$-Resin, and Modification by EL, Cleavage from Resin, and Deproduction of Side Chain (Experimental Procedure)

i) Deprotection of Mtt Group
Into a screw tube, 0.30 g of the peptide resin synthesized in 1 was charged, and to this was added excess amount of dichloromethane (DCM) and swollen over 30 minutes, then excess DCM was removed by a nitrogen gas. Thereafter, 4 ml of a mixed solution of DCM:TFA (trifluoroacetic acid):TIPS (triisopropylsilane)=94:1:5 was added and the mixture was stirred for 2 minute, and the solvent was removed by a nitrogen gas. This operation was repeated five times, and suction filtration was conducted. The residue was washed with DCM, triethylamine and DCM, then dried under reduced pressure.

ii) Modification by Methoxy Type Organic EL-Dye
To the peptide resin dried under reduced pressure, 6 mL of 1-methyl-2-pyrrolidone (NMP) was added, and the mixture was stirred for 30 minute to swell, and 0.15 ml of triethylamine was added and the mixture was stirred. Further, 0.2 g of the active ester (6) was added and the mixture was stirred at room temperature for 24 hours. Then, suction filtration was conducted, and the residue was washed with NMP and DCM and dried under reduced pressure.

iii) Cleavage from Resin and Deproduction of Side Chain
To the peptide resin dried under reduced pressure, 0.08 ml of m-cresol, 0.48 ml of thioanisole and 3.44 ml of TFA were added, and the mixture was stirred at room temperature for 1 hour. Then, the mixture was suction-filtrated and washed with TFA. TFA was distilled off under reduced pressure, and in an ice bath, 15 ml of ether was added. After treatment by ultrasound, the mixture was left for a while, and the supernatant was removed. Then, in an ice bath, 15 ml of ethyl acetate was added. After ultrasound treatment, the mixture was left for a while. Then, the mixture was filtrated under reduced pressure and washed with ether, and dried under reduced pressure.

Figure 6A:
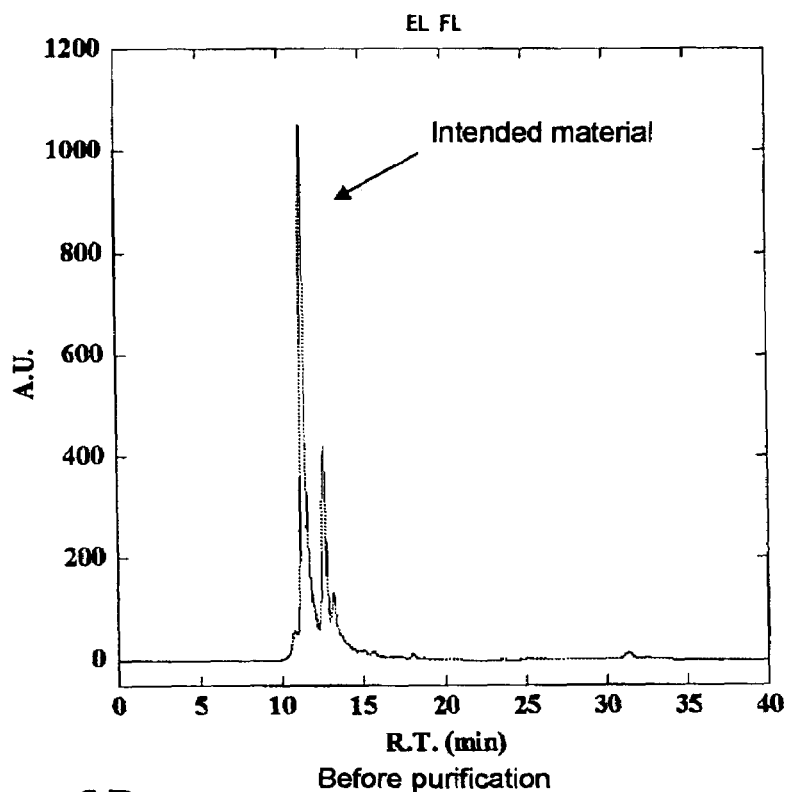
FIG. 6A shows one example of the HPLC profile of a labeled peptide in Example 3 of the present invention before purification.
Figure 6B:
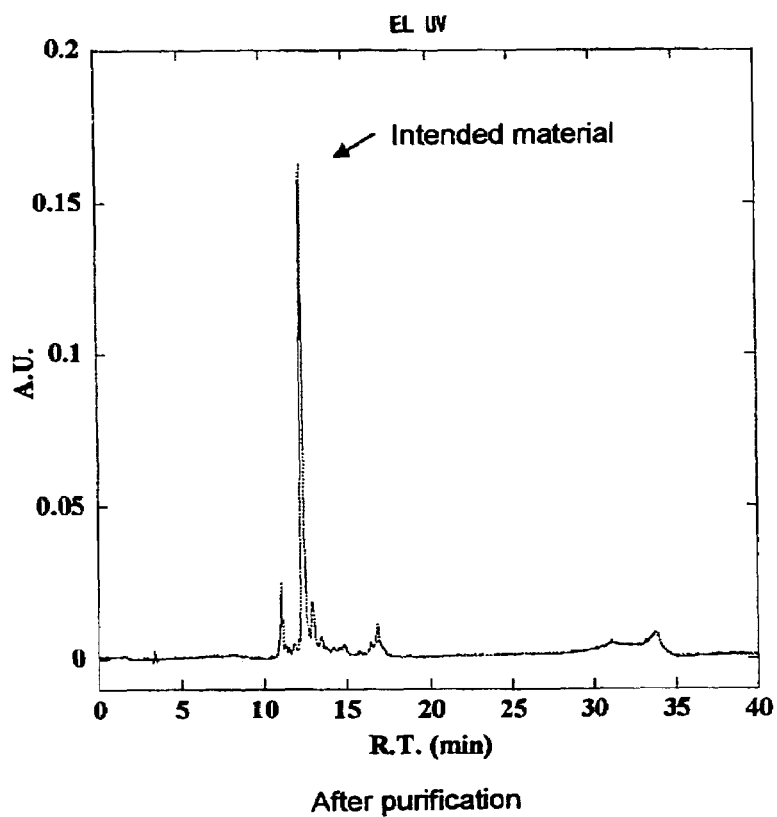
FIG. 6B shows one example of the HPLC profile of a labeled peptide in Example 3 of the present invention after purification.
Figure 7:
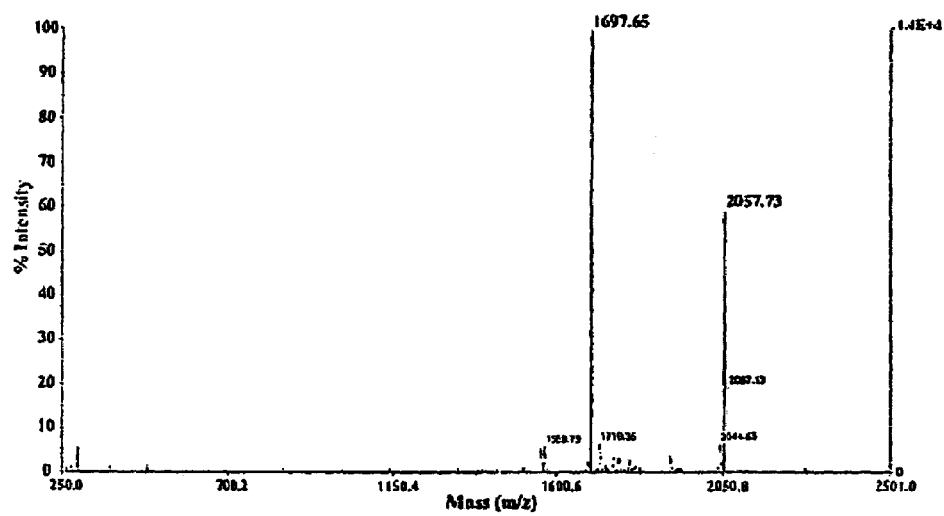
FIG. 7 shows one example of the TOF MS (Time of Flight Mass Spectrometry) spectrum of a labeled peptide in Example 3 of the present invention.

Orange color solid was obtained, and the yield was 0.29 g. HPLC prpfiles before purification and after purification of the product are shown in FIG. 6A and FIG. 6B, respectively. A sample showing a peak around R.T.=12.5 min was subjected to TOF-Mass measurement. As a result, a peak at 2057.33 was observed corresponding to a molecular weight of a complex of an EL-dye and peptide (EL-Peptide) of 2055.30, confirming the production of the intended material (Matrix: α-cyano-4-hydroxycinnamic acid (α-CHCA); FIG. 7)

2. Detection of Peptide
In the same manner as that of Example 1, a labeled peptide spotted on a glass substrate was detected. As the detection instrument, BIO-RAD molecule imager FX Pro was used. The laser wavelength was 488 nm and the scan interval was 50 nm.

Figure 8:
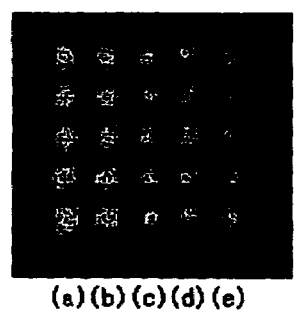
FIG. 8 shows one example of the emission pattern of a labeled peptide in Example 3 of the present invention, and (a), (b), (c), (d) and (e) show results of 10 fmol, 5 fmol, 1 fmol, 0.5 fmol and 0.1 fmol, respectively.

(Result)
FIG. 8 shows an emission pattern of the labeled peptide, and (a), (b), (c), (d) and (e) show emission patterns of 10 fmol, 5 fmol, 1 fmol, 0.5 fmol and 0.1 fmol, respectively. The detection limit of the relative concentration of the labeled peptide was 0.1 fmol (100 amol), and therefore, detection in high sensitivity was possible. The reaction of the peptide and EL-dye was almost quantitative.

EXAMPLE 4

<Labeling of Proteins with Dye, and Detection Thereof>

1. Labeling of Protein with Dye

An amino group of a lysine residue of bovine serum albumin (BSA) and an active ester of an organic EL-dye were reacted to form an amide bond for labeling of BSA. Specifically, to 58 μl of carbonate buffer (pH 9.0) containing 4.0 mg (58 nmol) of BSA was added 40 μl of a DMSO solution containing 3.6 mg (8.6 μmol) of an active ester of an organic EL-dye (EL-OSu) and the mixture was shaken at 37° C. for 24 hours. 0.1 M TEAA buffer (pH 7.0) was added so as to give the total volume of 1 ml, and components derived from BSA were separated using NAP-10 column (Pharmacia Sephadex G-25), and the separated solution was freeze-dried over night.

Figure 9A:
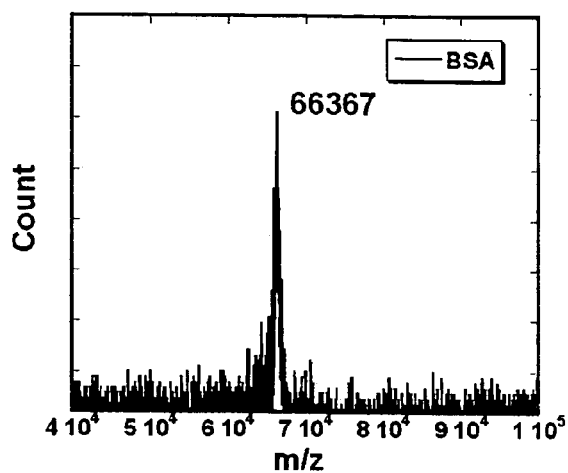
FIG. 9A shows one example of the TOF MS spectrum of a labeled protein in Example 4 of the present invention before labeling.
Figure 9B:
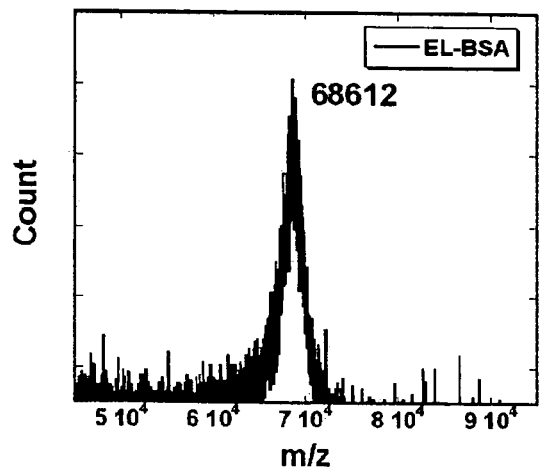
FIG. 9B shows one example of the TOF MS spectrum of a labeled protein in Example 4 of the present invention after labeling.

Identification of BSA labeled with an organic EL-dye was conducted by MALDI TOF MS. As shown in FIG. 9, the labeled BSA (FIG. 9B) had molecular weight increased by about 2200 as compared with the raw material (FIG. 9A), showing that about five organic EL-dyes was bonded thereto.

2. Detection of Protein (Result)

Figure 10:
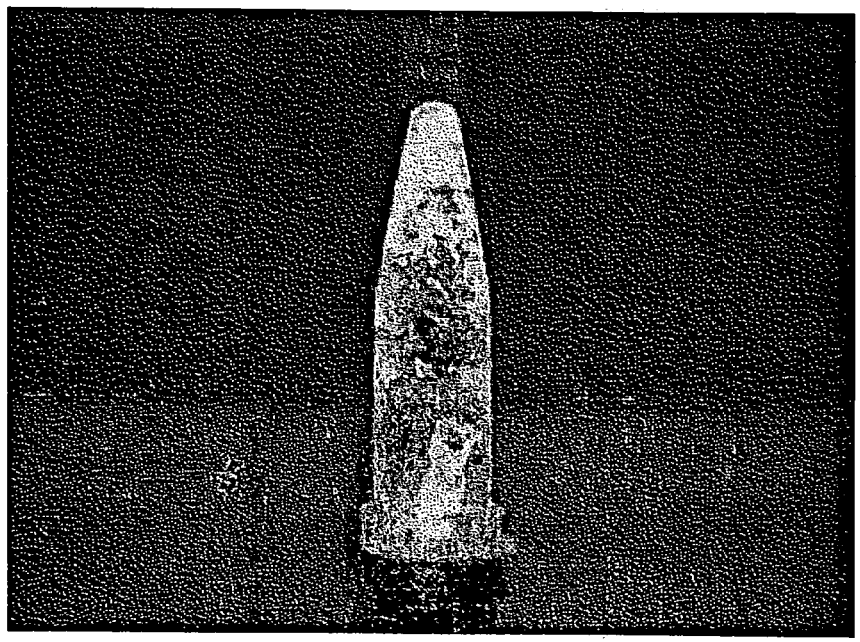
FIG. 10 shows one example of the emission pattern of a labeled protein in Example 4 of the present invention.

The prepared BSA emitted fluorescence in solid state as shown in FIG. 10. Thus, it was clarified that a protein can be labeled by an active ester of an organic EL-dye.

What is claimed is:

1. A method of detecting a biological molecule, comprising
reacting a sample containing the biological molecule with an organic electroluminescence dye (EL-dye), to label the biological molecule, and
measuring the fluorescence of the biological molecule which has been labeled with the organic EL-dye,
wherein the organic EL-dye is a compound selected from the group consisting of the following formula (1) to (6):

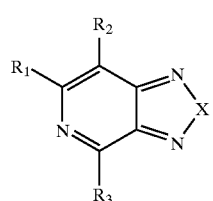

(1)

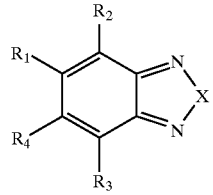

(2)

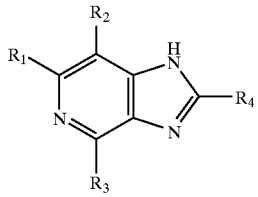

(3)

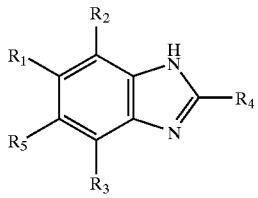

(4)

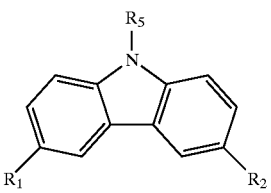

(5)

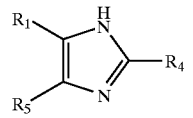

(6)

wherein,
$R_1$, $R_2$, $R_3$, $R_4$ and $R_5$ are each independently an aromatic hydrocarbon group, hydrocarbon group, heterocyclic group or aromatic group containing a hetero atom in the ring, optionally having a substituent selected from hydrogen atom, halogen atom, hydroxyl group, cyano group or sulfonyl group, and
X is a nitrogen atom, sulfur atom, oxygen atom, selenium atom or boron atom, optionally having a substituent.

2. The method according to claim 1, wherein the organic EL-dye and the biological molecule are bound by an amide bond, imide bond, urethane bond, ester bond, guanidine bond or thiourea bond.

3. The method according to claim 2, wherein prior to reacting the sample with the organic EL-dye, a reactive group selected from the group consisting of an isocyanate group, isothiocyanate group, epoxy group, halogenated alkyl group, triazine group, carbodiimide group and active ester carbonyl group, is introduced into the organic EL-dye.

4. The method according to claim 1, wherein the biological molecule is selected from the group consisting of nucleic acid, protein, peptide and saccharide.

5. A method of detecting a biological molecule comprising
reacting a sample containing the biological molecule with a labeling dye comprising an oxazolopyridine derivative, to label the biological molecule, and
measuring the fluorescence of the labeled biological molecule in the sample,
wherein the oxazolopyridine derivative is a compound of the following formula:

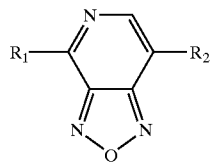

Formula 13 wherein,

R$_1$ and R$_2$ are each independently an aromatic hydrocarbon group, hydrocarbon group, heterocyclic group or aromatic group containing a hetero atom in the ring, optionally having a substituent selected from hydrogen atom, halogen atom, hydroxyl group, cyano group or sulfonyl group.

6. The method according to claim 5, wherein prior to reacting the sample with the labeling dye, a reactive group selected from the group consisting of an isocyanate group, isothiocyanate group, epoxy group, halogenated alkyl group, triazine group, carbodiimide group and active ester carbonyl group, is introduced into the labeling dye.

7. A labeling dye used for detection of a biological molecule by measurement of fluorescence, wherein the labeling dye comprises an organic EL-dye having a reactive group that binds to the biological molecule, wherein the organic EL-dye is a compound selected from the group consisting of the following formula (1) to (6):

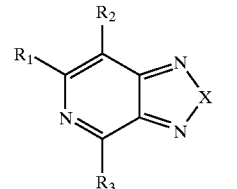

(1)

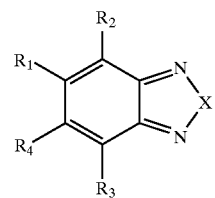

(2)

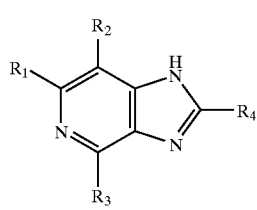

(3)

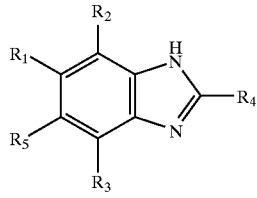

(4)

-continued

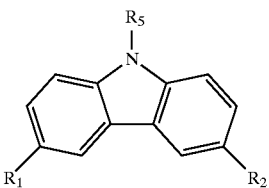

(5)

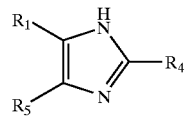

(6)

wherein,

R$_1$, R$_2$, R$_3$, R$_4$ and R$_5$ are each independently an aromatic hydrocarbon group, hydrocarbon group, heterocyclic group or aromatic group containing a hetero atom in the ring, optionally having a substituent selected from hydrogen atom, halogen atom, hydroxyl group, cyano group or sulfonyl group, and X is a nitrogen atom, sulfur atom, oxygen atom, selenium atom or boron atom, optionally having a substituent.

8. The labeling dye according to claim 7, wherein the organic EL-dye comprises an oxazolopyridine derivative of the following formula:

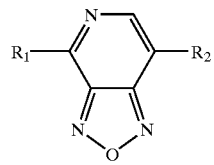

Formula 13 wherein,

R$_1$ and R$_2$ are each independently an aromatic hydrocarbon group, hydrocarbon group, heterocyclic group or aromatic group containing a hetero atom in the ring, optionally having a substituent selected from hydrogen atom, halogen atom, hydroxyl group, cyano group or sulfonyl group.

9. The labeling dye according to claim 7, wherein the reactive group is selected from the group consisting of a carboxyl group, isocyanate group, isothiocyanate group, epoxy group, halogenated alkyl group, triazine group, carbodiimide group and active ester carbonyl group.

10. A labeling kit for labeling a biological molecule, comprising an organic EL-dye for labeling the biological molecule, wherein the organic EL-dye is a compound selected from the group consisting of the following formula (1) to (6):

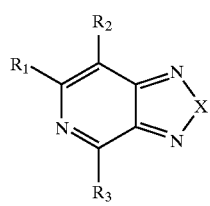

(1)

-continued (2) 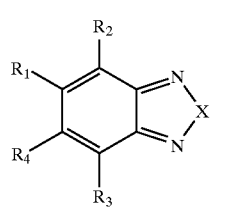

(3) 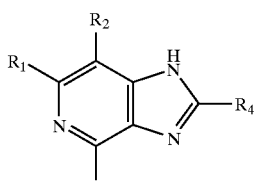

(4) 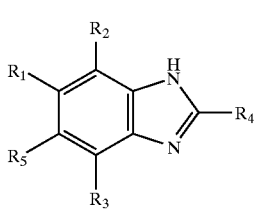

(5) 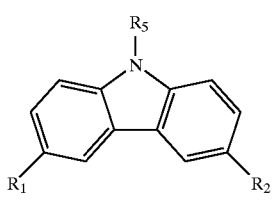

(6) 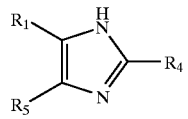

wherein, $R_1$, $R_2$, $R_3$, $R_4$ and $R_5$ are each independently an aromatic hydrocarbon group, hydrocarbon group, heterocyclic group or aromatic group containing a hetero atom in the ring, optionally having a substituent selected from hydrogen atom, halogen atom, hydroxyl group, cyano group or sulfonyl group, and X is a nitrogen atom, sulfur atom, oxygen atom, selenium atom or boron atom, optionally having a substituent.

11. The labeling kit according to claim 10, wherein the organic EL-dye comprises an oxazolopyridine derivative of the following formula:

Formula 13

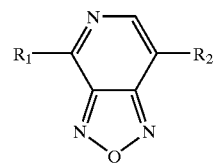

wherein, $R_1$ and $R_2$ are each independently an aromatic hydrocarbon group, hydrocarbon group, heterocyclic group or aromatic group containing a hetero atom in the ring, optionally having a substituent selected from hydrogen atom, halogen atom, hydroxyl group, cyano group or sulfonyl group.

12. The labeling kit according to claim 10, wherein the organic EL-dye comprises a reactive group selected from consisting of a carboxyl group, isocyanate group, isothiocyanate group, epoxy group, halogenated alkyl group, triazine group, carbodiimide group and active ester carbonyl group.

* * * * *